US00PP23207P3

(12) United States Plant Patent
Nielsen

(10) Patent No.: US PP23,207 P3
(45) Date of Patent: Nov. 20, 2012

(54) ***OSTEOSPERMUM* PLANT NAMED 'DAOSNITTEN'**

(50) Latin Name: *Osteospermum ecklonis*
Varietal Denomination: DAOSNITTEN

(75) Inventor: Rune Harboe Nielsen, Odense N (DK)

(73) Assignee: Dalina ApS, Odense N (DK)

( * ) Notice: Subject to any disclaimer, the term of this patent is extended or adjusted under 35 U.S.C. 154(b) by 38 days.

(21) Appl. No.: 13/064,616

(22) Filed: Apr. 4, 2011

(65) Prior Publication Data

US 2012/0255084 P1 Oct. 4, 2012

(51) Int. Cl.
*A01H 5/00* (2006.01)

(52) U.S. Cl. ..... Plt./360

(58) Field of Classification Search ..... Plt./360
See application file for complete search history.

(56) References Cited

OTHER PUBLICATIONS

Printout of application information from Community Plant Variety Office (CPCO) website for corresponding CPCO application No. 2010/0796 filed Apr. 6, 2010 (1 page) (http://www.cpvoextranet.cpvo.europa.eu).

Printout of application information from Canadian Food Inspection Agency—Plant Varieties Journal No. (date) for corresponding Canadian Plant Breeders' Rights application No. 10-6960 filed May 3, 2010 (1 page) (http://www.inspection.gc.ca/english/plaveg/pbrpov/joubule.shtml).

*Primary Examiner* — Susan McCormick Ewoldt
(74) *Attorney, Agent, or Firm* — Foley & Lardner LLP

(57) ABSTRACT

A new and distinct cultivar of *Osteospermum* plant named 'DAOSNITTEN', characterized by its vigorous growth, with globular upright to spreading shape; well branching (4-6 per plant) habit, with stiff and strong lateral stems and thick leaves (color of leaves RHS 139A (upper side) RHS 138A (underside)); big inflorescence with strong ray florets with unique color combination (RHS N80C with stripes of N80B) at the upper side, and inflorescence that stays open, even in cold and dark weather conditions.

5 Drawing Sheets

Latin name of the genus and species of the claimed plant: *Osteospermum ecklonis*.

Variety denomination: 'DAOSNITTEN'.

BACKGROUND OF THE INVENTION

The present invention relates to a new and distinct cultivar of *Osteospermum* plant, botanically known as *Osteospermum ecklonis* (DC) T Norl., commonly known as Cape Daisy and and hereinafter referred to by the cultivar name 'DAOSNITTEN'.

The new *Osteospermum* cultivar is a product of a planned breeding program conducted by the inventor, Rune Nielsen, in Stige, Denmark. The objective of the breeding program is to develop a new *Osteospermum* cultivar with good garden performance, well branching growth, continuous flowering and an attractive inflorescence color.

The new *Ostospermum* cultivar originated from a cross made in a controlled breeding program by the inventor in 2007, in Stige, Denmark. The female or seed parent is *Osteospermum* variety designated 2045F (not patented). The male or pollen parent is a creme coloured *Osteospermum* variety designated 2010A (not patented).

Asexual reproduction of the new *Osteospermum* cultivar by terminal cuttings was first performed in November, 2008 in Stige, Denmark, and has demonstrated that the combination of characteristics as herein disclosed for the new cultivar are firmly fixed and retained through successive generations of asexual reproduction. The new cultivar reproduces true to type.

BRIEF SUMMARY OF THE INVENTION

The following traits have been repeatedly observed and are determined to be unique characteristics of 'DAOSNITTEN', which in combination distinguish this *Osteospermum* as a new and distinct cultivar:

1. Vigorous cultivar, with globular upright to spreading shape;
2. Well branching (4-6 per plant) with stiff and strong lateral stems and thick leaves. Color of leaves RHS 139A (green) (upper side) RHS 138A (green) (Underside);
3. Big inflorescence with strong ray florets with unique color combination (RHS N80C (purple-violet) with stripes of N80B (purple-violet)) at the upper side; and
4. Inflorescence that stays open even in cold and dark weather conditions.

Plants of the new *Osteospermum* 'DAOSNITTEN' differ from plants of the parents, 2045F (unpatented) and 2010A (unpatented) in the traits described in Table 1.

TABLE 1

Comparison with Parental Varieties

| Trait | New Cultivar 'DAOSNITTEN' | Female Parent 2045F (unpatented) | Male Parent 2010A (unpatented) |
|---|---|---|---|
| Plant Size | | | |
| Height: | About 11 cm. | About 12 cm. | About 11 cm. |
| Diameter: | About 17 cm. | About 16 cm. | About 15 cm. |

TABLE 1-continued

| Comparison with Parental Varieties | | | |
|---|---|---|---|
| Trait | New Cultivar 'DAOSNITTEN' | Female Parent 2045F (unpatented) | Male Parent 2010A (unpatented) |
| Overall Plant Shape: | Globular, upright to spreading, with basal branching. | Globular, upright to spreading, with basal branching. | Globular, upright to spreading, with basal branching. |
| Stem | | | |
| Length: | About 6 cm. | About 7 cm. | About 5 cm |
| Diameter: | About 4 mm | About 3 mm. | About 5 mm. |
| Strength: | Stiff and strong. | Medium strong. | Stiff and strong. |
| Color: | RHS 144A (yellow-green) | RHS 144A (yellow-green) | RHS 146D (yellow-green). |
| Number of Inflorescence heads per Plant: | About 30. | About 30. | About 20. |
| Flower Size Diameter: | About 8.5 cm. | About 7 cm. | About 8 cm. |
| Mature Petal Color (upper surface): | RHS N80C (purple-violet) with stripes of N8OB (purple-violet). | RHS 73A (red-purple), with stripes of 75B (purple). N79A (purple) near base. | RHS N81C (purple-violet) with stripes of 76C (purple) |

Of the many commercial cultivars known to the present inventor, the most similar in comparison to the new *Osteospermum* 'DAOSNITTEN' is the *Osteospermum* cultivar 'Cape Daisy® Kalanga Lavender', in the characteristics described in Table 2.

TABLE 2

| Comparison with Comparison Varieties | | |
|---|---|---|
| Trait | New Cultivar 'DAOSNITTEN' | Comparison Cultivar 'Cape Daisy ® Kalanga Lavender' |
| Plant Size | | |
| Height: | About 11 cm. | About 9 cm. |
| Diameter: | About 17 cm. | About 16 cm. |
| Overall Plant Shape: | Globular, upright to spreading, with basal branching. | Globular, upright to spreading, with basal branching. |
| Branches | | |
| Length: | About 6 cm. | About 5 cm. |
| Diameter: | About 4 mm. | About 4 mm. |
| Strength: | Stiff and strong. | Medium strength. |
| Color: | RHS 144A (yellow-green). | RHS 145C (yellow-green). |
| Number of Inflorescence heads per Plant: | About 30. | About 30. |
| Flower Size Diameter: | About 8.5 cm. | About 6.5 cm. |
| Mature Petal Color (upper surface): | RHS N80C (purple-violet) with stripes of N80B. | RHS N80B (purple-violet). |
| Inflorescence head open during cold and low light conditions: | Fully open. | Closed to partly open. |

BRIEF DESCRIPTION OF THE PHOTOGRAPHS

The accompanying photographs illustrate the overall appearance of the new *Osteospermum* 'DAOSNITTEN' showing the colors as true as is reasonably possible with colored reproductions of this type. Colors in the photographs may differ slightly from the color value cited in the detailed botanical description, which accurately describe the color of 'DAOSNITTEN'.

DETAILED BOTANICAL DESCRIPTION

Figure 1:
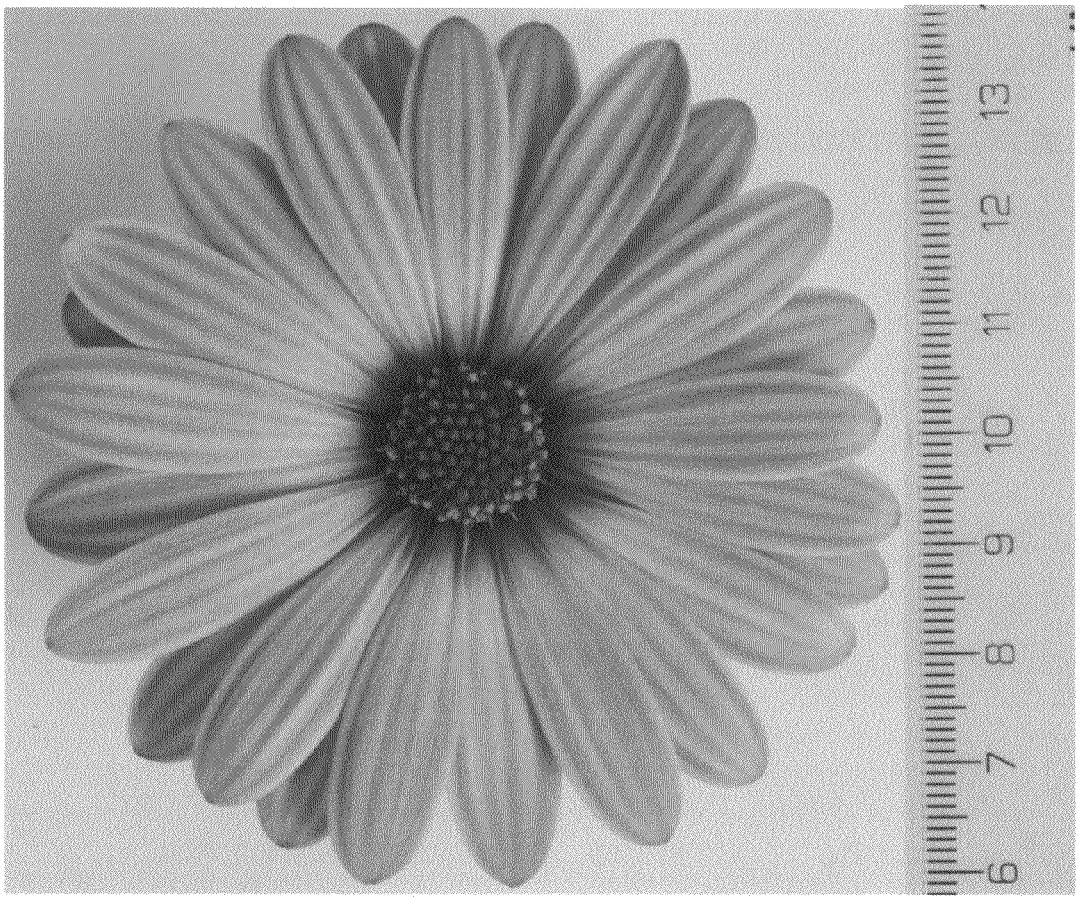
FIG. 1 shows a close-up view of the composite flower head from 'DAOSNITTEN'.
Figure 2:
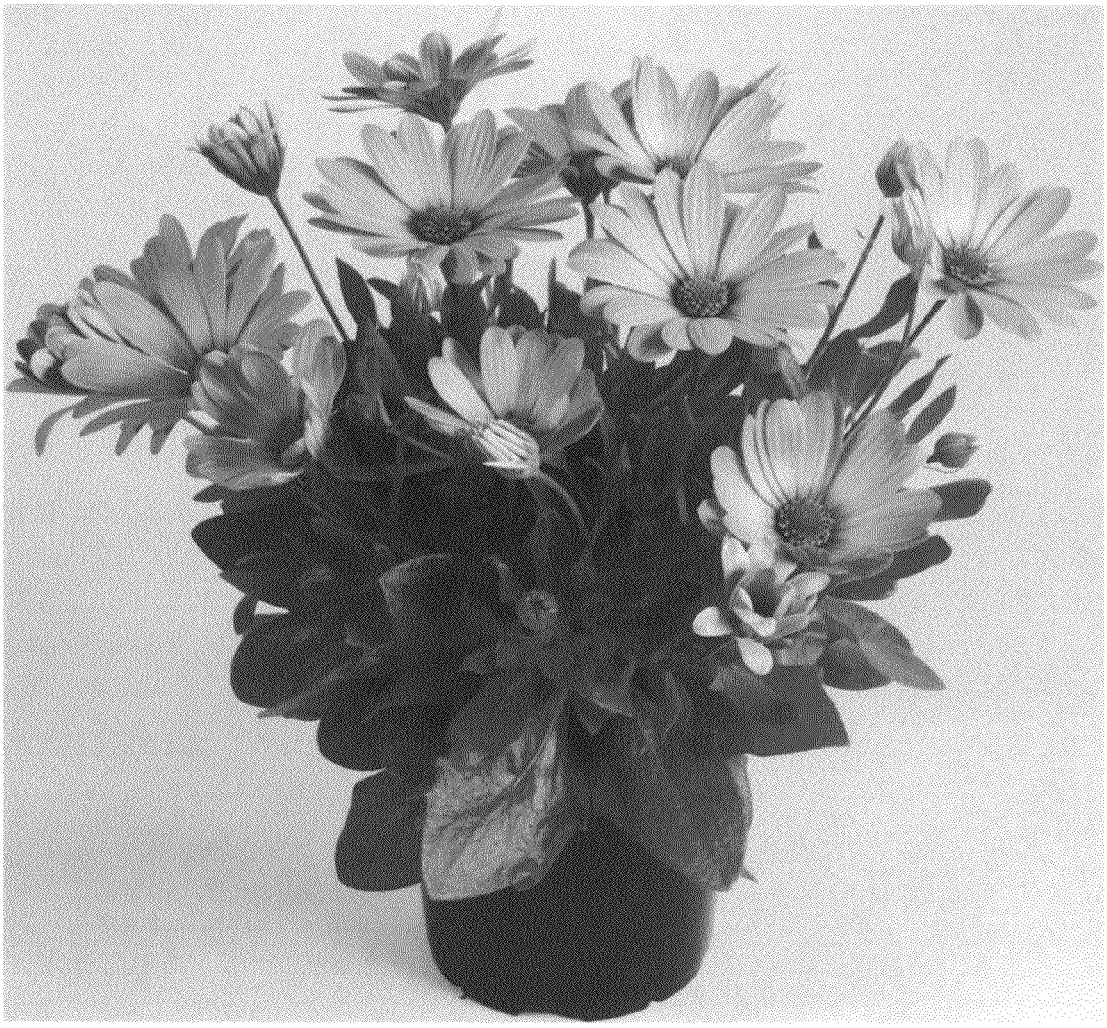
FIG. 2 shows a side view perspective of a typical flowering plant of 'DAOSNITTEN' in a 11 cm pot, at 12 weeks of age after planting.
Figure 3:
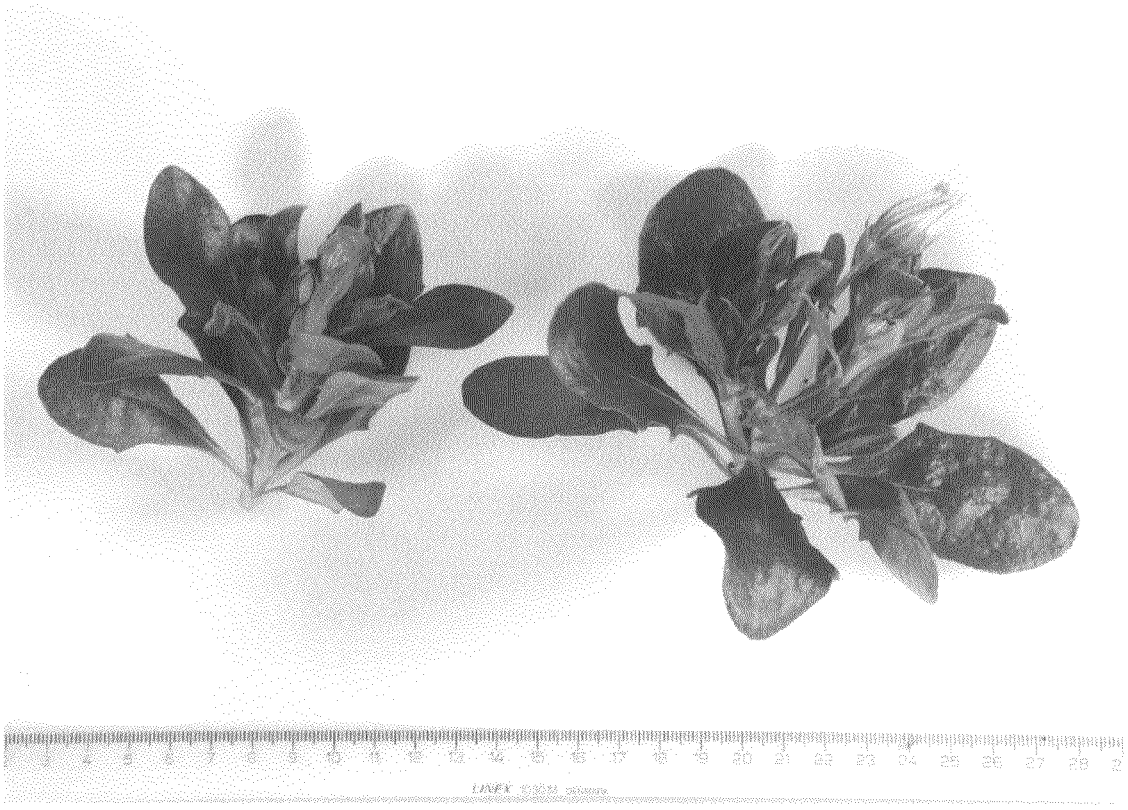
FIG. 3 shows a close-up view of the typical lateral stems with leaves and buds of 'DAOSNITTEN'.
Figure 4:
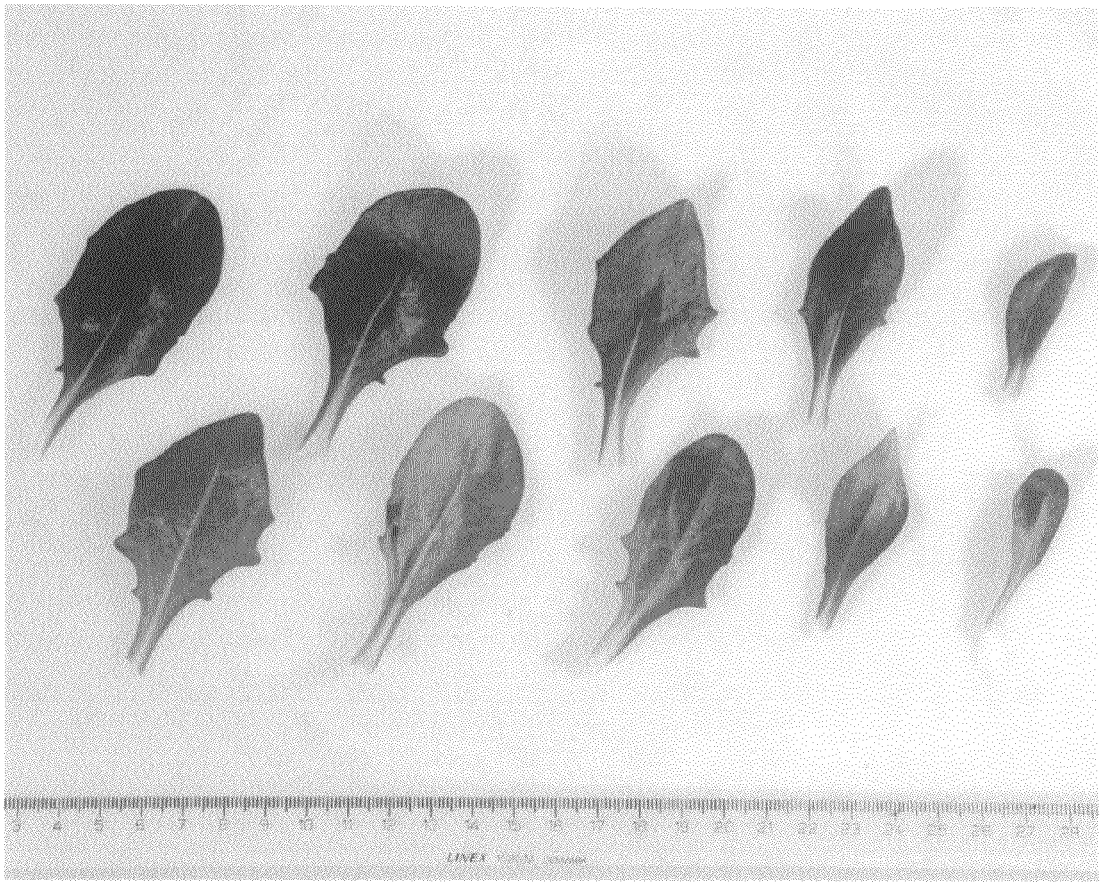
FIG. 4 shows a close-up view of the different leaf sizes of 'DAOSNITTEN'.
Figure 5:
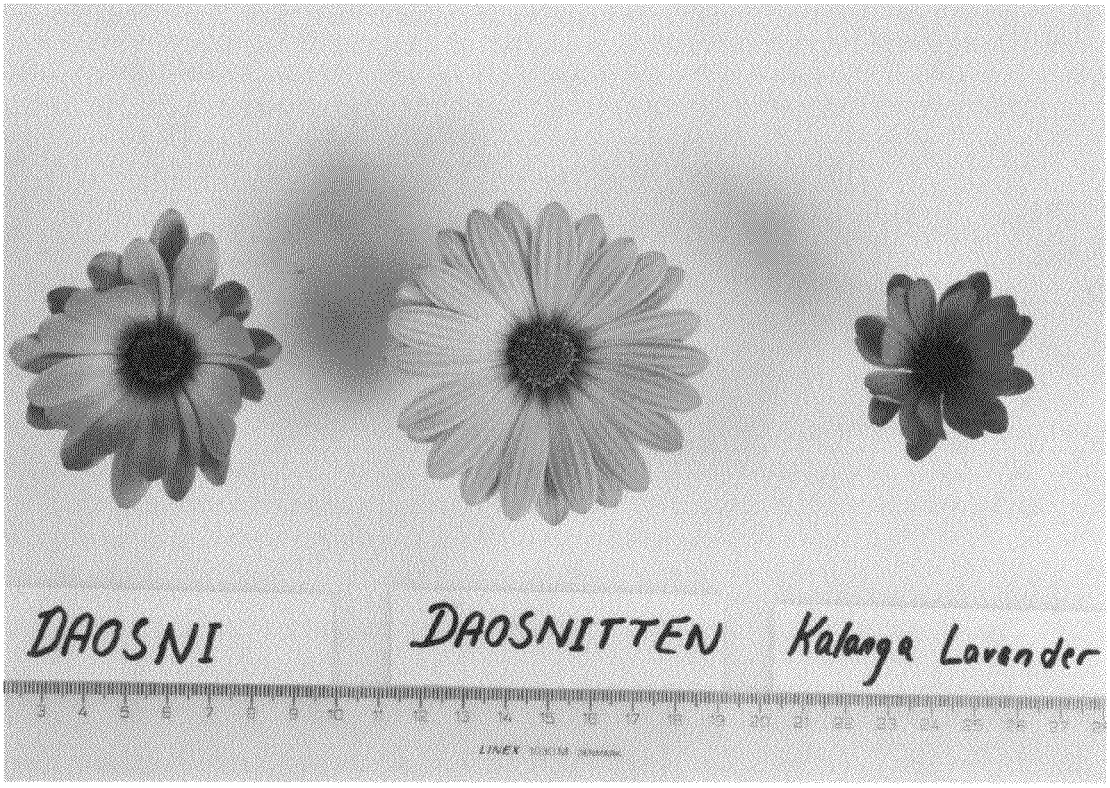
FIG. 5 shows a comparison between 'DAOSNI', 'CAPE DAISY® Kalanga Lavender' and 'DAOSNITTEN', (Breeders reference: 6415H).

The new *Osteospermum* 'DAOSNITTEN' has not been observed under all possible environmental conditions. The phenotype of the new cultivar may vary with variations in environment such as temperature, light intensity, and day length without any change in the genotype of the plant.

The aforementioned photographs, together with the following observations, measurements and values describe the new *Osteospermum* 'DAOSNITTEN' as grown in a glasshouse, equipped with heat, assimilation light and ebb/flood watering system in Odense, Denmark, under conditions which closely approximate those generally used in commercial practice. The plants was grown in 14° C., with a venting temperature on 16° C. Assimilation light was given when natural daylight was below 3000 lux and the day length was extended to 16 hours. The EC levels in the soil, was kept at about 2.5-3.5 and pH around 6.0 during the production. Plant growth was regulated 3 times during the production period, using 3‰ Cycocel (chlormequat-chloride) as a drench (80-100 ml/pot).

Color references are made to The Royal Horticultural Society Colour Chart (R.H.S.), Colour Chart 2001 edition, Color values were taken under March daylight conditions at approximately 10:00-14:00 in Stige, Denmark. The age of the 'DAONITTEN' plants described is 12 weeks from potting.

Classification:

*Botanical.*—*Osteospermum ecklonis* (DC) Norl.

Parentage:

*Female or seed parent.*—*Osteospermum* variety designated 2045F (unpatented).

*Male or pollen parent.*—*Osteospermum* variety designated 2010A (unpatented).

Propagation:

*Type.*—Vegetative terminal cuttings.

*Time and temperature to initiate roots.*—About 9 to 13 days at 19 to 21° C. in tunnels in a greenhouse.

*Time and temperature to produce a rooted young plant.*—About 4 to 5 weeks at 18° (initiation period benefits from 19-21° C.).

*Rooting habit.*—Vigorous, white to grayed yellow and well branched.

Plant description:

*General appearance and form.*—Globular, upright, with basal branching. Inflorescences in composite heads. Freely branching with lateral flowering branches forming at every node.

*Growth rate.*—Growing about 1 cm per week during production period.

*Plant height*.—About 11 cm to 14 cm.

*Plant width* (*spread*).—About 15 cm to 18 cm.

*Crop time to produce a mature flowering plant*.—It requires 4-5 weeks to produce a young plant in a 35 mm propagation plug. After potting 12-14 weeks are required to produce finished flowering plants in 11 cm pots.

Stem:

*Shape*.—Round.

*Length*.—About 5 cm to 7 cm.

*Diameter*.—About 4 mm to 5 mm.

*Strength*.—Stiff and strong.

*Aspect*.—Upright.

*Texture*.—Smooth and glabrous.

*Color*.—Mature: RHS 144A. Immature: RHS 144B.

Branches:

*Branching habit*.—Basal branching with lateral branching.

*Number of branches per plant*.—About 4-6.

*Length* (*including flowers*).—About 13 cm to 15 cm.

*Diameter*.—About 4 mm.

*Strength*.—Stiff and strong.

*Apect*.—Upright to spreading.

*Texture*.—Smooth and glabrous.

*Color*.—Mature: RHS 144A. Immature: RHS 144B.

*Internode length*.—About 1 to 10 mm.

*Internode color*.—RHS 144A.

Foliage description:

*Arrangement*.—Alternate.

*Number of leaves per branch*.—About 10 to 14 per branch.

*Length*.—About 6 cm to 8 cm.

*Width*.—About 2 cm to 4 cm.

*Overall shape of leaf*.—Obovate to spatulate with 2 to 4 acuminate teeth.

*Shape at apex*.—Obtuse.

*Shape at base*.—Attenuate.

*Margin*.—Dentate (2 lobes on each side of leaf).

*Texture*.—Upper surface: Pubescent with few scattered short, stiff hairs. More hairs on the edges of leaf. Lower surface: Pubescent with few scattered short, stiff hairs. More hairs along veins and on the edges of leaf.

*Color of developing foliage*.—Upper surface: RHS 139B. Lower surface: RHS 138A.

*Color of mature foliage*.—Upper surface: RHS 139A. Lower surface: RHS 138A.

*Venation pattern*.—Trinerved with veins along nerves.

*Venation color*.—Upper surface: RHS 145A. Lower surface: RHS 144B.

Inflorescence description:

*Arrangement and shape*.—Tubular disc floret and flat, lanceolate ray florets in composite flower heads, developed from terminal and axillary shoots. The peduncles lift the Inflorescences 2-4 cm above the foliage. Inflorescences face upright to 70° angle from vertical.

*Natural flowering season*.—*Osteospermum* is a bedding plant, with a flowering season from early spring to late autumn. Temperatures below 20° C. will increase flowering, temperatures above 20° C. will reduce flowering.

*Time to flower*.—65 to 85 days.

*Inflorescence longevity on the plant*.—Inflorescence will maintain good color and substance for about 5-10 days; however, the longevity of individual inflorescence is highly dependent on temperature and light conditions. Inflorescence persistent.

*Quantity of inflorescences heads*.—Freely flowering; about 30 buds and open inflorescences per plant.

*Fragrance*.—Sweet, fresh and discreet.

*Bud* (*inflorescences head*).—Rate of opening (from showing color to fully open flower): 1 to 5 days. The rate of opening is highly dependent on temperature and light conditions. Length: About 12 mm. Diameter: About 10 mm. Shape: Acuminate. Texture: Pubescent with small hairs. Color: RHS 144A at base to 144B at apex.

*Peduncle*.—From both terminate and axillary shoots. Length: About 6 cm. Diameter: About 2 mm. Angle: About 0-30° from vertical. Strength: Stiff and strong. Texture: Pubescent with small white hairs. Color: RHS 138A.

*Inflorescence head*.—Length: About 10 mm. Diameter: About 8,5 cm.

*Ray florets*.—Quantity per Inflorescence head: 19-23. Length: 40 mm. Widths: 10-12 mm. Overall shape: Spatulate. Shape at apex: Obtuse. Shape at base: Acute. Margin: Entire. Texture: Upper surface: smooth, matt, slightly furrowed. Lower surface: smooth, matt slightly furrowed. Color upper side: RHS N80C with stripes of N80B. Color underside: RHS 92D with stripes of 92A.

*Disc florets*.—Quantity per Inflorescence head: 65-75. Length: 8 mm. Diameter: 1 mm. Color RHS 96A white at base.

*Phyllary*.—Quantity per Inflorescence head: 15 - 20. Length: 8-10 mm. Width: 1-3 mm. Overall shape: Lanceolate. Apix: Narrow Acuminate. Base: Fused. Margin: Entire. Color: RHS 144A.

Reproductive organs:

*Androecium*.—Location: Disc florets only. Stamen number: 5 fused. Stamen length: About 2 mm. Anther shape: Linear, fused. Anther length: About 2 mm. Pollen amount: Medium amount. Pollen color: RHS N25C.

*Gynoecium*.—Location: Ray and disc florets. Quantity: 1. Pistil length: About 5 mm. Stigma shape: Brush-like, cleft 2 mm deep. Stigma length: About 2 mm. Stigma color: RHS 103A. Style length: About 2 mm. Style color: RHS 103C. Ovary color: RHS 144D.

Seed/fruit: Seed and fruit production has not been observed.

Disease/pest resistance: Resistance to pathogens and pests common to *Osteospermum* has not been observed.

Disease/pest susceptibility: Susceptibility to pathogens and pests common to *Osteospermum* has not been observed.

Temperature tolerance: Plants of the new *Osteospermum* have exhibited good tolerance rain, wind and drought; however, flowering may cease during hot periods (temperatures above 25° C.). Low temperature tolerance to 1° C.

What is claimed is:

1. A new and distinct cultivar of *Osteospermum* plant named 'DAOSNITTTEN', as illustrated and described herein.

* * * * *